(12) United States Patent
Henselmans

(10) Patent No.: US 11,058,376 B2
(45) Date of Patent: Jul. 13, 2021

(54) ADJUSTABLE SUPPORT

(71) Applicant: Elekta Limited, West Sussex (GB)

(72) Inventor: Rens Henselmans, West Sussex (GB)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 16/540,227

(22) Filed: Aug. 14, 2019

(65) Prior Publication Data
US 2020/0054296 A1   Feb. 20, 2020

(30) Foreign Application Priority Data

Aug. 15, 2018 (GB) .................................... 1813324

(51) Int. Cl.
  *A61N 5/00* (2006.01)
  *A61B 6/00* (2006.01)
  *A61N 5/10* (2006.01)

(52) U.S. Cl.
  CPC .............. *A61B 6/44* (2013.01); *A61N 5/1081* (2013.01)

(58) Field of Classification Search
  USPC ..................................................... 250/492.1
  See application file for complete search history.

(56) References Cited

U.S. PATENT DOCUMENTS

| | | | |
|---|---|---|---|
| 7,014,361 B1 | 3/2006 | Ein-gal | |
| 9,313,867 B2 * | 4/2016 | Sharpless | ................ F16C 27/00 |
| 9,700,741 B2 * | 7/2017 | Arber | .................. A61N 5/1081 |
| 10,016,171 B2 * | 7/2018 | Fortuna | .................. A61B 6/508 |
| 10,610,175 B2 * | 4/2020 | Maurer, Jr. | .......... A61N 5/1081 |
| 10,772,590 B2 * | 9/2020 | Arber | ................. G01R 33/4808 |
| 2004/0005027 A1 | 1/2004 | Näfstadius | |
| 2004/0184579 A1 | 9/2004 | Mihara et al. | |
| 2012/0027183 A1 | 2/2012 | Sharpless et al. | |
| 2012/0189102 A1 | 7/2012 | Maurer, Jr. et al. | |
| 2012/0205555 A1 | 8/2012 | Dirauf et al. | |
| 2013/0158382 A1 | 6/2013 | Chao | |
| 2014/0171725 A1 | 6/2014 | Adler et al. | |
| 2014/0205059 A1 | 7/2014 | Sharpless et al. | |
| 2017/0239496 A1 | 8/2017 | Sun et al. | |

FOREIGN PATENT DOCUMENTS

| | | | |
|---|---|---|---|
| EP | 2741672 A2 | 6/2014 | |
| EP | 3281674 A1 | 2/2018 | |
| WO | WO-03008986 A2 | 1/2003 | |
| WO | WO-2014045095 A2 | 3/2014 | |

OTHER PUBLICATIONS

"United Kingdom Application Serial No. 1813324.9, Search Report dated Feb. 4, 2019", (Feb. 4, 2019), 4 pgs.
"European Application Serial No. 19190608.0, European Search Report dated Feb. 7, 2020", (Feb. 7, 2020), 14 pgs.

* cited by examiner

*Primary Examiner* — Phillip A Johnston
(74) *Attorney, Agent, or Firm* — Schwegman Lundberg & Woessner, P.A.

(57) ABSTRACT

An adjustable support for a gantry for a radiotherapy apparatus, wherein the support comprises a base and a mounting member for supporting a gantry, wherein the position of the mounting member relative to the base is adjustable.

19 Claims, 4 Drawing Sheets

ADJUSTABLE SUPPORT

CLAIM FOR PRIORITY

This application claims the benefit of priority of United Kingdom Application No. 1813324.9, filed Aug. 15, 2018, which is hereby incorporated by reference in its entirety.

TECHNICAL FIELD

The present patent document relates to an adjustable support for a rotatable gantry, in particular, to an adjustable support for a rotatable gantry forming part of an image guided radiation therapy (IGRT) apparatus.

BACKGROUND

Radiation therapy is a localised treatment designed to treat an identified tissue target (such as a cancerous tumour) and spare the surrounding normal tissue from receiving doses above specified tolerances thereby minimising risk of damage to healthy tissue. Prior to delivery of radiation therapy, an imaging system can be used to provide a three dimensional image of the target from which the target's size and mass can be estimated and an appropriate treatment plan determined.

Many factors may contribute to differences between the dose distribution determined in the treatment plan and the delivered dose distribution. One such factor is an inconsistency between the patient position at the imaging stage and the patient position during radiation therapy treatment.

Image guided radiation therapy (IGRT) involves the use of an imaging system to view target tissues prior to or whilst radiation treatment is being delivered to the target tissue. IGRT incorporates imaging coordinates from the treatment plan to ensure that the patient is properly aligned for treatment during radiation therapy treatment.

Various medical imaging technologies are used to identify target tissues in radiation therapy planning and IGRT. These include (without limitation); Computed Tomography (CT), Positron Emission Tomography (PET), Ultrasound imaging and Magnetic Resonance Imaging (MRI).

The Applicant's prior published international patent application no. WO03/008986 describes a device for use in IGRT which includes the functions of an MRI device in a radiation therapy treatment apparatus and proposes technology for overcoming the problems in doing so.

The device comprises a large rotating ring gantry onto which a linear accelerator is mounted and arranged to travel around a target positioned at the isocentre of the ring. An MRI sits in the aperture of the ring gantry sharing the isocentre. A body to be treated is introduced into a treatment space at the isocentre by means of a sliding table.

The gantry is rotatably mounted and held on a static ring. The static ring is mounted on a base and, together with the base, forms a support assembly for the gantry.

When providing an apparatus as described above, it is important for the position of the gantry to be adjustable so that the gantry and magnet are aligned. This ensures that the X-ray beam is directed through the gap in the magnet where there is less material to attenuate the beam. Without correct alignment, there is potential for attenuation, scatter and the magnetic field being affected.

SUMMARY

In view of the fact that fine positional adjustment is needed once the various components of the gantry are installed in place, it is particularly problematic to provide a support assembly, which is not only able to cope with the large forces involved, but which also allows the required fine positional adjustment of the gantry. For example, when the IGRT gantry support is assembled and built into a pit in the treatment room, it is particularly challenging to allow access for adjustments to be made.

The present systems and methods can help to alleviate these problems.

According to one aspect of the present disclosure, there is provided an adjustable support for a gantry for a radiotherapy apparatus, wherein the support comprises a base and a mounting member for supporting a gantry, wherein the position of the mounting member relative to the base is adjustable.

Preferably the base and the mounting member are joined together by one or more flexible plates.

Preferably, the base and the mounting member are joined together by one or more resilient plates.

Preferably, the base and the mounting member are joined together by one or more plate springs.

Preferably, the base and the mounting member are joined together by one or more leaf springs.

It is to be understood that, in the context of the present disclosure, the terms "plate spring" and "leaf spring" are used interchangeably.

Preferably, the adjustable support comprises at least two flexible plates, wherein at least one flexible plate is placed on a first lateral side of the base and at least one flexible plate is positioned on an opposing second lateral side of the base.

The present approach provides a significant improvement in the fine adjustment of the static ring in three degrees of freedom (y, $R_x$, $R_z$). The present approach thus allows for the gantry and the magnet of the IGRT apparatus to be accurately aligned to ensure that the X-ray beam is directed through the gap in the magnet where there is less material to attenuate the beam, which ensures that unwanted attenuation and scatter is avoided. The fine adjustment enabled by the present invention allows for improved installation of the IGRT apparatus and also allows for ease of access in subsequent service and maintenance.

Preferably, the mounting member comprises a static ring for supporting a rotatable gantry.

The provision of flexible plates, plate springs, or leaf springs, is such that the position of the mounting member/static ring relative to the base can be adjusted accurately and with ease.

Preferably, the one or more flexible plates are positioned in a vertical orientation.

It is understood that "vertical" orientation refers to the longest dimension of the flexible plate and the z-axis or z-direction, which is the axis substantially perpendicular to the treatment room floor when the gantry is installed in a treatment room.

It is understood that the y-axis or y-direction refers to the axis running substantially in the direction from the front to back or back to front of the static ring and the base. The x-axis or x-direction is understood to refer to the axis running substantially in the direction from side to side of the static ring and the base.

Preferably, the support comprises at least one adjustment mechanism for altering the position of the mounting member relative to the base.

Preferably, the support comprises at least one flexible plate positioned on a first lateral side of the base with a first adjustment mechanism attached thereto and at least one flexible plate is positioned on an opposing second lateral side of the base with a second independent adjustment mechanism attached thereto.

Preferably, the adjustment mechanism moves the one or more flexible plates in the y-direction.

Preferably, the adjustment mechanism permits the one or more flexible plates to be rotatable about the x-axis and/or about the z-axis.

The adjustable support of the present disclosure is alignable in three degrees of freedom to ensure accurate alignment.

Preferably, the or each flexible plate resists or prevents movement of the adjustable support in the x-direction and/or the z-direction.

Preferably, the or each flexible plate resists or prevents rotation about the y-axis.

Preferably, the or each flexible plate spring has high stiffness in the x-direction and/or the z-direction.

This orientation of the flexible plate/s and the arrangement of the adjustment mechanism allows the flexible plates to permit forward and rearward movement of the mounting member in a "y-direction" whilst, at the same time, supporting the load of a gantry provided on the mounting member in the vertical, "z-direction" and in a sideways, or "x-direction". The plate spring is compliant in the out-of-plane direction to allow for the adjustment and tilt about the rotational axis $R_x$ and $R_y$.

It has been found that the adjustable support of the present disclosure is able to withstand the rotations about the $R_x$ and $R_y$ axis of rotation that occur during adjustment of the support.

Preferably, each of the one or more flexible plates comprises one or more mounting member connectors for connecting the flexible plate to the mounting member and one or more base connectors for connecting the flexible plate to the base.

Preferably, the connectors comprise one or more bolts.

Preferably, the connectors comprise one or more push-pull bolts.

Preferably, the or each push-pull bolt exerts a force on the or each flexible plate in a y-direction.

Preferably, the or each push-pull bolt is lockable.

Preferably, the or each push-pull bolt is concentric with an adjuster bushing through which a locking bolt is inserted.

It is understood that reference to a "push-pull bolt" refers to a mechanism by which rotation of the bolt compresses or relaxes the or each flexible plate in a direction substantially parallel to the y-axis.

Preferably, the support comprises one or more clamps for clamping the one or more flexible plates into engagement with the base and/or the mounting member.

Preferably, the one or more clamps comprise a clamping plate for receiving one or more bolts and for securing at least one flexible plate between the clamping plate and the base or mounting member.

Preferably, the clamping plate comprises a plurality of apertures for alignment with a plurality of apertures on the base or mounting member, said apertures for receiving one or more bolts.

Preferably, the or each flexible plate is held in place by at least one clamping plate with multiple bolts installed through the or each clamping plate.

A clamping plate having multiple bolts achieves a high clamping force and ensures that the stack of clamping plates and flexible plates are securely clamped together. Multiple bolts ensure that a high contact force is achieved.

Preferably, the support comprises a pair of flexible plates.

Preferably, the mounting member comprises legs for engagement with the base.

Preferably, the mounting member comprises a pair of legs.

Preferably, each of said legs comprises one or more of said flexible plates.

Preferably, the one or more flexible plates are positioned on a front face of the support.

Preferably, the position of the adjustment mechanism is at a location accessible from the floor level of the treatment room.

When the adjustable support for a gantry is assembled, it is built into a pit in the treatment room/radiation bunker floor. The present approach allows for the adjustment mechanism to be moveable to allow for access during maintenance and repair.

Preferably, the adjustment mechanism comprises a threaded adjuster rotatable within a screw-thread of the base and moveable through the base via rotation of the adjuster and into abutment with the mounting member.

This allows fine adjustment of the position of the mounting member relative to the base because, as the adjuster is rotated within the screw-thread of the base in a first direction it gradually moves into abutment with the mounting member. Once in abutment with the mounting member, further movement of the adjuster causes the adjuster to "push" the mounting member into a different position.

Preferably, the adjuster comprises a convex abutment surface for abutment with the mounting member. This is particularly advantageous because it means that contact between the adjuster and the mounting member is maintained even if the vertical orientation of the mounting member is changed, for example if the mounting member is pivoted forward or backward slightly. This is, therefore, particularly advantageous in combination with an adjustable upper support, as described in further detail below.

Preferably, the mounting member comprises an abutment ring for abutment with the adjuster. Preferably, the abutment ring is a conical ring.

Preferably, the abutment ring is a bronze abutment ring.

Preferably, the adjuster is connected to the mounting member such that rotation of the adjuster in a second direction causes the adjuster to "pull" the mounting member into a different position.

Preferably, the adjuster comprises a connector, preferably a cap, for engagement with the mounting member, preferably a front face of the mounting member.

Preferably, the adjuster is a threaded sleeve. Alternatively, the adjuster is a bolt.

Preferably, the adjustment mechanism comprises a lock for locking the position of the mounting member relative to the base.

Preferably, the lock comprises a bolt which passes through the base.

Preferably, the lock comprises a bolt which passes through the base and the mounting member.

Preferably, the lock comprises a nut for engagement with the end of the bolt and for tightening the mounting member into engagement with the adjuster.

Preferably, the adjuster is a sleeve and the lock comprises a bolt positioned within the sleeve.

Preferably, the sleeve comprises a screw-thread on its inner surface for engagement with the screw-thread of the bolt.

This concentric arrangement of a threaded sleeve for adjusting the position of the mounting member and a bolt positioned and rotatable within the sleeve is particularly advantageous because it securely locks the sleeve, base and mounting member in position. Such a rigid "lock" is particularly important in the context of the present invention, where it is important to maintain the position of the components of the gantry for optimum performance.

Preferably, the adjuster is a stainless-steel adjuster.

Preferably, the base comprises one or more mating parts for engagement with one or more mating parts on the mounting member.

Preferably, the base comprises one or more protrusions for engagement with one or more recesses on the mounting member.

For example, in a preferred embodiment, the base comprises first and second protrusions for engagement with first and second recesses of the mounting member; preferably, wherein the first recess is provided on the underside of a first leg of the mounting member and the second recess is provided on the underside of a second leg of the mounting member.

The provision of the respective mating parts on the base and mounting member is advantageous because it prevents the mounting member from "tipping off" the base.

Preferably, the base and mounting member are positioned such that a gap is provided therebetween. This allows for adjustment of their relative positions and also limits the adjustment range.

Preferably, the gap permits forward and rearward movement of the mounting member relative to the base.

Preferably, the adjuster is positioned within an aperture of the protrusion of the base. Preferably, the adjuster is positioned for abutment or connection with a wall of the recess of the mounting member.

Preferably, a wall of the recess of the mounting member comprises an aperture for receiving the adjuster or for connection thereto.

As such, in a preferred embodiment of the present disclosure, the adjustment mechanism comprises (i) a threaded sleeve rotatable within a threaded aperture of a protrusion of the base, and (ii) a threaded bolt rotatable within the threaded sleeve, the threaded bolt moveable through an aperture of a wall of a recess of the mounting member.

Preferably, the threaded bolt is received within a screw thread of a nut or block positioned on the mounting member.

Preferably, the support comprises one or more clamps; preferably, clamping plates and the threaded bolt is received within an aperture of the clamp/clamping plate. Preferably, the aperture comprises a screw-thread or is for engagement with a screw-thread.

Preferably, the clamp; more preferably the clamping plate, comprises a protrusion or block with a screw-threaded aperture for receiving the threaded bolt.

Preferably, the support further comprises an upper securing means; preferably, a wall or ceiling securing member; for example, an arm.

Preferably, the upper securing means is adjustable; preferably, the upper securing means is adjustable in length.

Preferably, the upper securing means is for connection to a wall and/or a ceiling.

Preferably, the base comprises an adjustment member for adjusting the gap between the base and the mounting member.

Preferably, the adjustment member comprises a rotatable bolt on the base; preferably, the adjustment member comprises a rotatable bolt on an upper surface of the base.

Preferably, the adjustment member is for abutment with a base surface of the mounting member. As such, once the mounting member has been lowered onto the base, it abuts the adjustment member. The height of the mounting member can then be altered by rotating and so lowering the adjustment member, which, in turn, allows the flexible plates to be aligned with the mounting member.

Preferably, the base and/or the mounting member comprise one or more guides for correct positioning of one or more of said flexible plates.

Preferably, the one or more guides comprise one or more recesses.

The provision of guides allows correct alignment of the flexible plates relative to the base and mounting member. In turn, this allows correct and accurate positioning of the base relative to the mounting member via accurate mechanical interfaces.

According to another aspect of the present disclosure, there is provided an image guided radiation therapy (IGRT) apparatus comprising an adjustable support as described herein supporting a rotatable gantry, said gantry comprising a medical imaging device and a radiation source.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the disclosure described herein and vice versa.

It will be appreciated that reference to "one or more" includes reference to "a plurality".

BRIEF DESCRIPTION OF THE DRAWINGS

An embodiment of the invention will now be described with reference to the accompanying Figures in which.

DETAILED DESCRIPTION OF THE DRAWINGS

Figure 1:
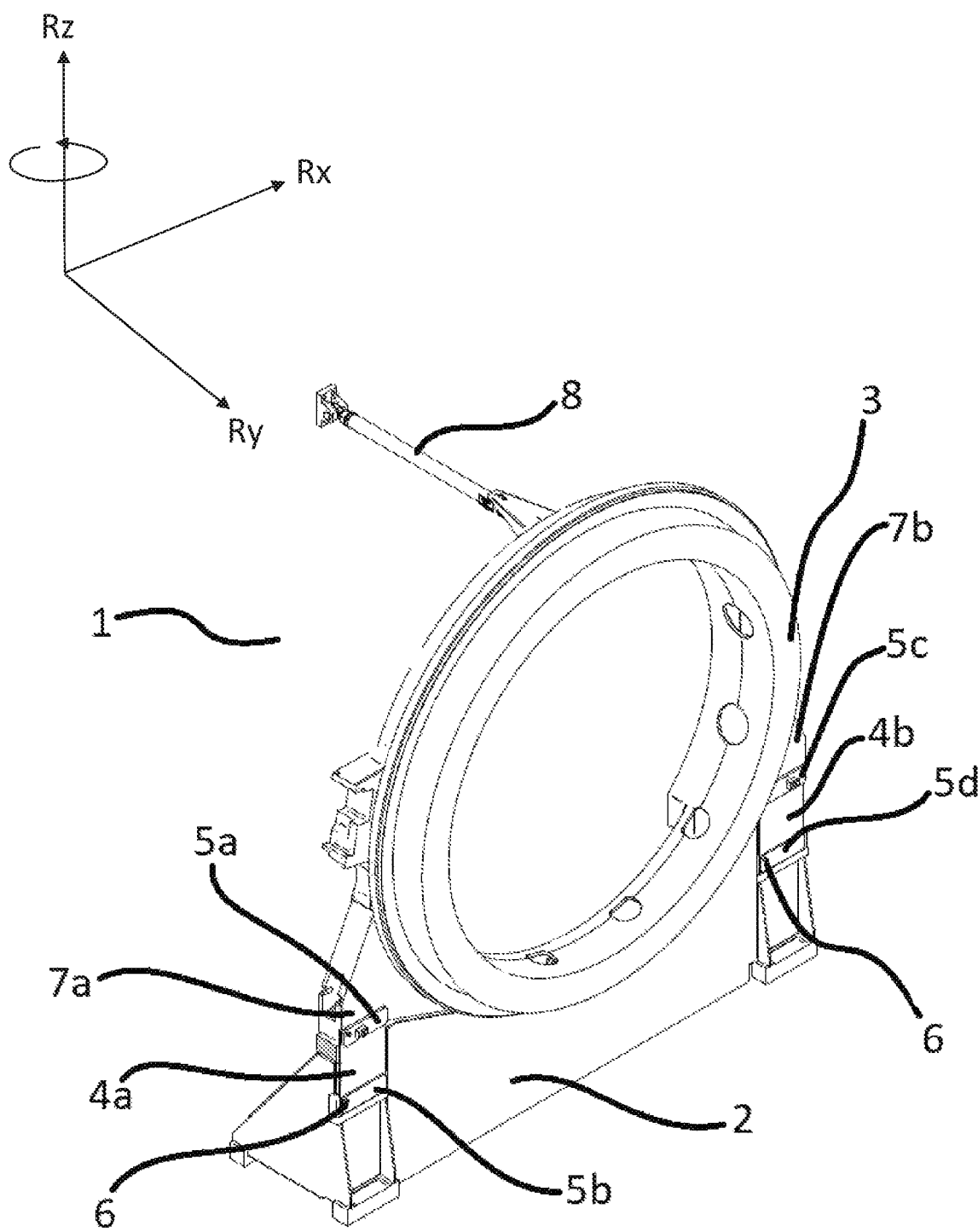
FIG. 1 shows a perspective view of a support in accordance with the present disclosure.
Figure 2A:
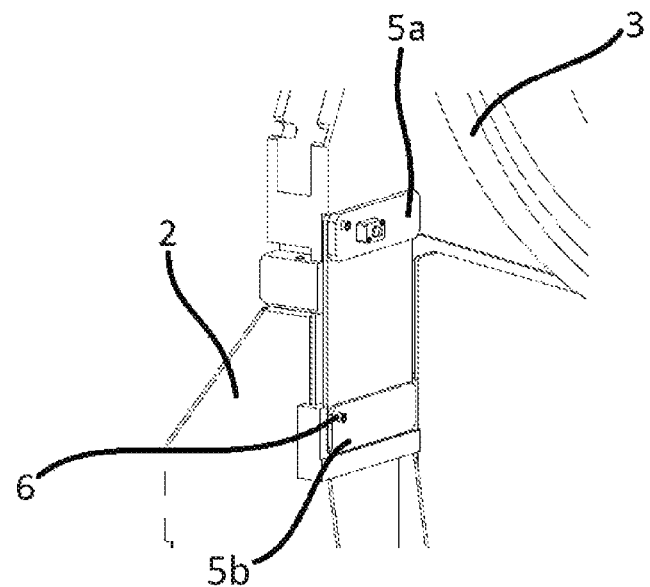
FIG. 2a and FIG. 2b show a flexible plate and abutment between the base and mounting member in further detail.
Figure 2B:
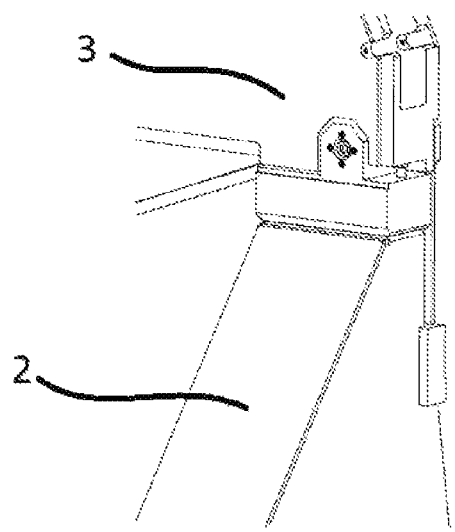

FIG. 1 shows an adjustable support 1 for a gantry (not shown). The support 1 comprises a base 2 and a mounting member 3 for supporting a gantry. In the example shown, the mounting member 3 is a static ring for rotatably supporting a dynamic gantry.

The support 1 includes a pair of plate springs 4a, 4b. The plate springs 4a, 4b permit forward and rearward movement of the static ring 3 in a "y-direction" whilst, at the same time, supporting the load of a gantry positioned on the static ring to restrict or prevent movement in the vertical, "z-direction" and rigidly supporting the static ring 3 in a sideways, or "x-direction".

Each plate spring 4a, 4b is secured to the base 2 and static ring 3 by clamping plates 5a, 5b, 5c, 5d. A plurality of bolts 6 pass through the clamping plates 5a, 5b, 5c, 5d and into engagement with screw-threads on the base 2 and static ring 3 to securely clamp the plate springs 4a, 4b in position. The plate springs 4a, 4b are secured to legs 7a, 7b of the static ring 3.

It has been found that a 300 mm×300 mm×10 mm aluminium plate provides the required range of movement and stiffness. The plate springs 4a, 4b have high in-plane stiffness; that is, they have resistance to deformation in response to an applied force. The plate springs 4a, 4b have sufficient strength to survive earthquakes. The plate springs 4a, 4b are compliant in the out-of-plane direction to allow for the adjustment and tilt about the rotation axis Rx and Rz of the static ring by elastic deformation. The plate springs 4a, 4b sit inside a mechanical fit and are held in place by the clamping plates 5a, 5b, 5c, 5d with multiple bolts 6 to achieve a high clamping force. The mechanical fit on the front face of the base 2 and static ring 3 also ensures that the static ring 3 position is constrained relative to the base 2 during assembly.

A wall support 8, in the form of an arm, is provided at the top of the static ring 3 for securing the upright position of the static ring relative to a wall (not shown). The "top" of the static ring 3 is understood to refer to the region of the static ring 3 which is furthest from the treatment room floor.

Figure 3:
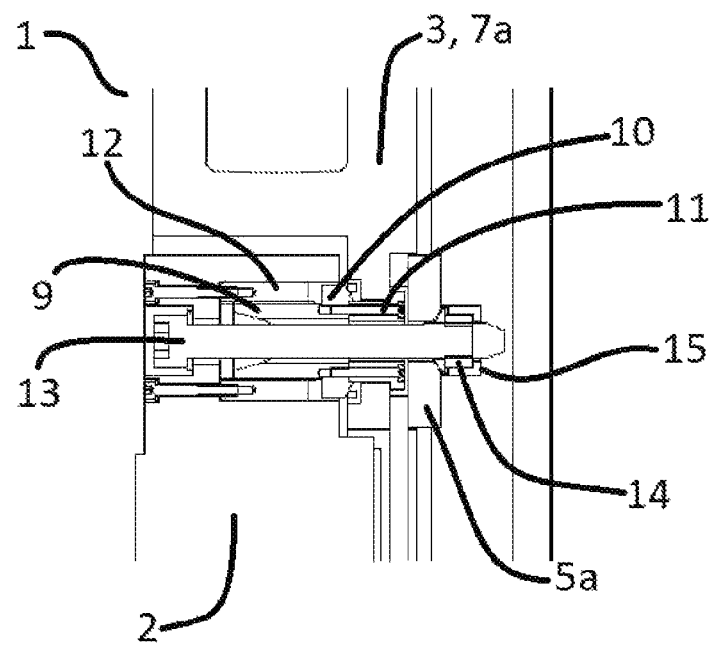
FIG. 3 shows a cross-sectional view showing the adjusting mechanism.

With particular reference to FIG. 3, the support 1 includes an adjustment mechanism 9 for altering the position of the static ring 3 relative to the base 2. In the example shown, the adjustment mechanism comprises a threaded sleeve/bush 9 rotatable within a screw-thread of the base 2. As the threaded sleeve/bush 9 is rotated, it moves into abutment with the static ring 3. Once in abutment with the static ring 3, further movement of the threaded sleeve/bush 9 pushes the static ring 3 into a different position.

The threaded sleeve/bush 9 comprises a convex abutment surface 10 for abutment with the static ring 3. Contact between the threaded sleeve/bush 9 and the static ring 3 is maintained even if the vertical orientation of the static ring 3 is changed. FIG. 3 also shows the provision of a cap 11 for pulling the static ring 3 into a different position.

Whilst in alternative embodiments, the screw-thread of the base 2 with which the sleeve/bush 9 engages is provided integrally with the walls of an aperture formed within the base 2, in the present example, an additional threaded bushing 12 is provided within an aperture of the base 2.

In the example shown, a locking bolt 13 is provided to lock the position of the static ring 3 relative to the base 2. The bolt 13 passes through the sleeve/bush 9 and through an aperture in the leg 7a of the static ring 3. Referring to FIGS. 3 and 5c, a nut 14 is provided within a block 15 on the clamping plate 5a.

When the nut 14 is tightened, this securely locks the position of the static ring 3 relative to the base 2.

Whilst the locking method could instead take the form of a pair of push-pull bolts, it has been found that these introduce a local moment when tightening, tend to shift during locking, and the locking pre-load is difficult to predict. This problem is overcome by the use of the concentric arrangement shown.

Figure 4:
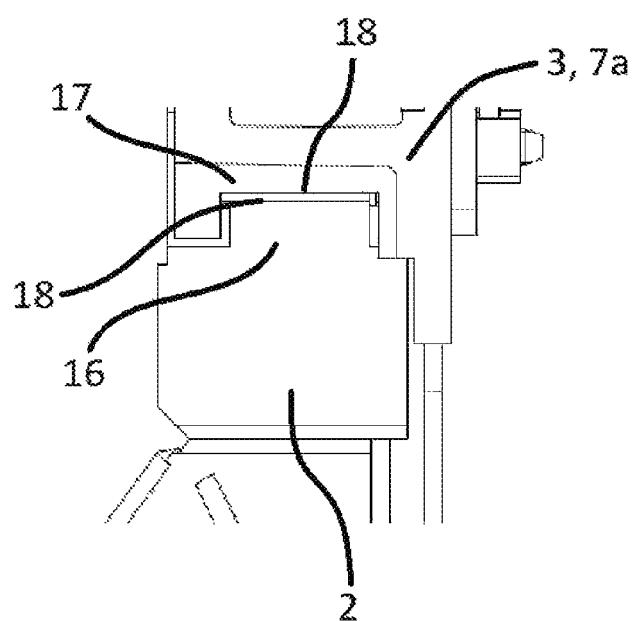
FIG. 4 shows a cross-sectional view showing the mating arrangement of the base and mounting member.

With particular reference to FIG. 4, the base 2 comprises a protrusion 16 which mates with a recess 17 provided on the underside of the leg 7a of the static ring 3. The provision of the respective mating parts on the base 2 and static ring 3 prevents the static ring 3 from "tipping off" the base 2 and also help to position the static ring 3 above the base 2.

Figure 5A:
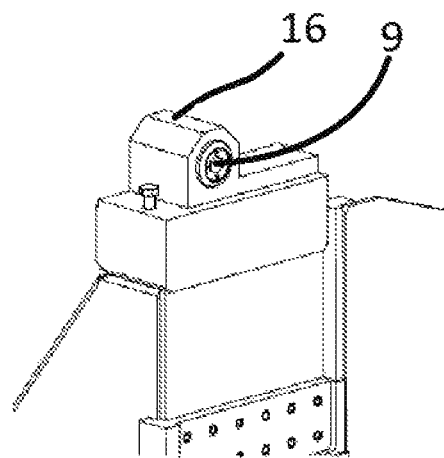
FIGS. 5a to 5c show the base protrusion, mounting member recess and clamp plate in further detail.
Figure 5B:
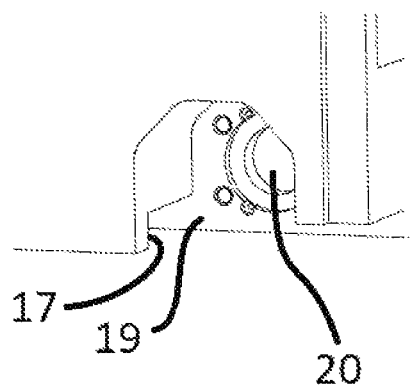
Figure 5C:
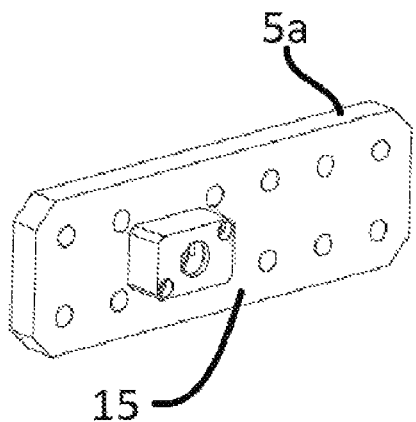

As shown with particular reference to FIGS. 3, 5a and 5b, the threaded sleeve 9 is positioned within the protrusion 16 of the base 2 and the front wall 19 of the recess 17 has an aperture 20 through which the locking bolt 13 can pass for connection to the nut 14 in the block 15 provided on the front facing surface of the clamping plate 5a.

Referring to FIG. 4, the base 2 and static ring 3 are positioned such that a gap 18 is provided therebetween. This allows for adjustment of their relative positions.

Further embodiments and simple design variations of the embodiments disclosed herein will no doubt occur to the skilled addressee without departing from the true scope of the claims of the invention as defined in the appended claims.

The invention claimed is:

1. An adjustable support for a gantry for a radiotherapy apparatus, wherein the support comprises a base and a static mounting member for supporting a rotatable ring gantry, wherein the position of the static mounting member relative to the base is adjustable, wherein the support comprises an adjustment mechanism for adjusting the position of the static mounting member relative to the base.

2. An adjustable support gantry for a radiotherapy apparatus according to claim 1, wherein the base and mounting member are joined together by one or more flexible plates.

3. An adjustable support according to claim 1, wherein the base and mounting member are joined together by one or more leaf springs.

4. An adjustable support for a gantry according to claim 1, wherein the mounting member comprises a static ring for supporting a rotatable gantry.

5. An adjustable support for a gantry according to claim 2, wherein the one or more flexible plates are positioned in a vertical orientation.

6. An adjustable support for a gantry according to claim 2, wherein the mounting member comprises a pair of legs and each of said legs comprises one or more of said flexible plates.

7. An adjustable support for a gantry according to claim 2, wherein the one or more flexible plates are positioned on a front face of the support.

8. An adjustable support for a gantry according to claim 1, wherein the position of the adjustment mechanism is at a location accessible from the floor level of the treatment room.

9. An adjustable support for a gantry according to claim 1, wherein the adjustment mechanism comprises a threaded adjuster rotatable within a screw-thread of the base and moveable through the base via rotation of the adjuster and into abutment with the mounting member.

10. An adjustable support for a gantry according to claim 9, wherein the adjuster comprises a convex abutment surface for abutment with the mounting member.

11. An adjustable support for a gantry according to claim 9, wherein the mounting member comprises an abutment ring for abutment with the adjuster.

12. An adjustable support for a gantry according to claim 11, wherein the abutment ring is a conical ring.

13. An adjustable support for a gantry according to claim 9, wherein the adjuster is connected to the mounting member such that rotation of the adjuster in a second direction causes the adjuster to "pull" the mounting member into a different position.

14. An adjustable support for a gantry according to claim 9, wherein the adjuster comprises a cap for engagement with a front face of the mounting member.

15. An adjustable support for a gantry according to claim 1, wherein the adjustment mechanism comprises a lock for locking the position of the mounting member relative to the base.

16. An adjustable support for a gantry according to claim 2, wherein the base and/or the mounting member comprise one or more guides for correct positioning of one or more of the flexible plates.

17. An adjustable support for a gantry according to claim 1, wherein the gantry is rotatable, in combination with an image guided radiation therapy (IGRT) apparatus that comprises a medical imaging device and a radiation source.

18. An adjustable support for a gantry for a radiotherapy apparatus, wherein the support comprises a base and a mounting member for supporting a gantry, wherein the position of the mounting member relative to the base is adjustable, the adjustable support comprising an adjustment mechanism, the adjustment mechanism including a threaded member rotatable with respect to a screw-thread of the base.

19. An adjustable support for a gantry for a radiotherapy apparatus, wherein the support comprises a base and a mounting member for supporting a gantry, wherein the position of the mounting member relative to the base is adjustable by adjustment of one or more flexible plates and wherein the base and the mounting members are joined together by one or more flexible plates.

\* \* \* \* \*